United States Patent [19]

Masters et al.

[11] Patent Number: 4,941,881
[45] Date of Patent: Jul. 17, 1990

[54] IV INFUSION SET WITH SHEATH

[76] Inventors: Edwin J. Masters, 142 Autumn, Sikeston, Mo. 63801; Paul L. Ebaugh, Chateau Girardeau, 3120 Independence, Cape Girardeau, Mo. 63701

[21] Appl. No.: 397,320
[22] Filed: Aug. 23, 1989
[51] Int. Cl.$^5$ ............................................. A61M 5/32
[52] U.S. Cl. ................................... 604/162; 604/177
[58] Field of Search .............. 604/177, 162, 171, 198, 604/263, 192

[56] References Cited

U.S. PATENT DOCUMENTS 3,910,272 10/1975 Forberg ........................ 604/162 X
4,631,058 12/1986 Raines ................................ 604/177
4,676,783 6/1987 Jagger et al. ........................ 604/177

Primary Examiner—John D. Yasko
Attorney, Agent, or Firm—Senniger, Powers, Leavitt and Roedel

[57] ABSTRACT

An improved IV infusion set of the type comprising a length of tube with a hollow needle at one end. The improvement comprises a sheath slidably disposed on the tube and adapted to be slid over the needle to cover the needle after use. The sheath is particularly adapted for use with IV infusion sets of the type comprising outwardly projecting flexible wings adjacent the end of the tubing with the needle, commonly referred to as "butterfly" infusion sets. The sheath comprises a hollow generally tubular body having a slot extending longitudinally from the forward end of the body partway toward the rearward end, and a cutout in the body at the rearward end of the slot. The slot allows the wings to pass to the cutout to allow at least a portion of the sheath to slide past the wings to cover the needle. The cutout engages the wings, locking the body in its position covering the needle. The sheath may be temporarily secured, for example by friction fit with some part of the infusion set, so that it does not interfere with the use of the infusion set.

19 Claims, 2 Drawing Sheets

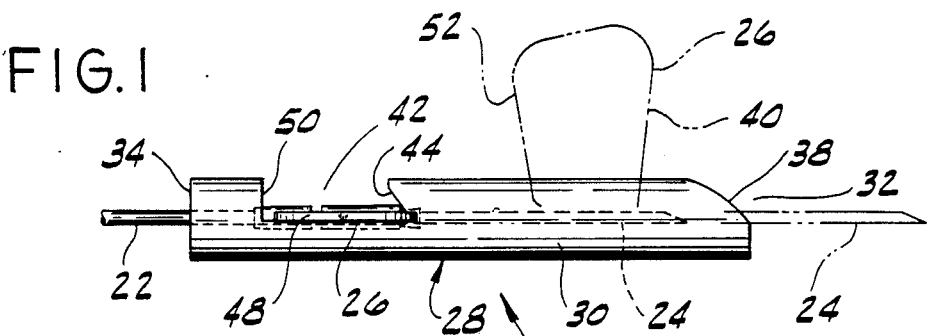
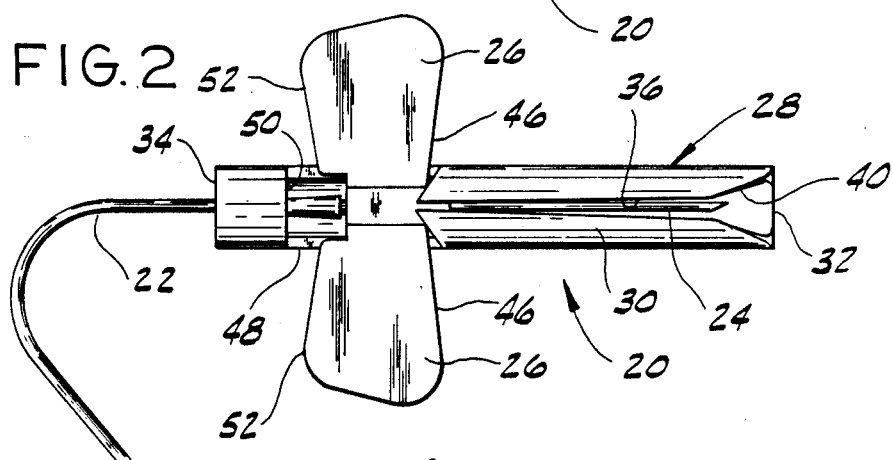
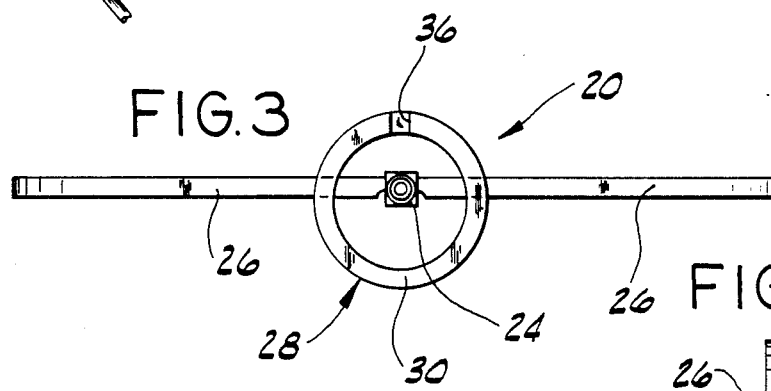
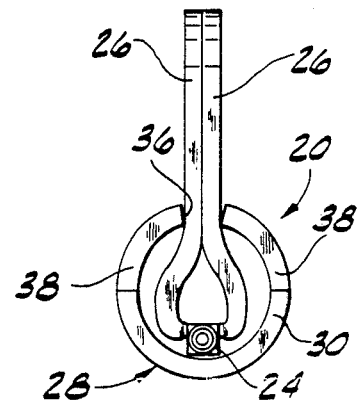

IV INFUSION SET WITH SHEATH

BACKGROUND OF THE INVENTION

This invention relates to intravenous (IV) infusion sets, and in particular to an IV infusion set with a protective sheath to prevent accidental needlesticks from such infusion sets.

Accidental needlesticks from contaminated medical equipment such as syringes and IV equipment pose a serious risk to health care professionals. Even maintenance personnel who dispose of the used medical equipment are at risk. Hepatitis and AIDS and other diseases can be, and sometimes are, transmitted by accidental needlesticks from needles used on infected patients.

Attempts have been made to combat the problem of accidental needlesticks from syringes. See for example the devices disclosed in our prior U.S. Pat. Nos. 4,654,034, 4,681,567, and 4,740,204. However until the present invention little, if anything, has been done to prevent needles sticks from IV equipment.

SUMMARY OF THE INVENTION

Among the objects of the present invention is the provision of an improved IV infusion set with means to cover the needle after it is used in order to reduce the risk of needlesticks, and in particular to provide an improved IV infusion set with a slidable sheath that covers the needle after it used. It is further among the objects of this invention to provide such an IV infusion set in which the sheath can be locked in its position covering the needle. It is also among the objects of at least some embodiments of this invention to provide an IV infusion set in which the needle can be retracted into a protective sheath by pulling on the IV tube.

Generally, the improved IV infusion set according to the present invention comprises a length of tube having a hollow needle at one end of the tube. A sheath is slidably disposed on the tube and is adapted to be slid over the needle to cover the needle after it has been used. The sheath includes means for locking the sheath in its position covering the needle to prevent needlesticks from the used needle.

The IV infusion set is preferably of the type having outwardly projecting flexible wings adjacent the needle, and the means for locking the sheath preferably comprises means for engaging the wings. The sheath preferably comprises a hollow generally tubular body having a forward end oriented toward the needle and a rearward end oriented away from the needle. The body has at least one longitudinally extending slot extending from the forward end of the body toward the rearward end. The slot is adapted to receive the wings to allow at least part of the sheath to be slid past the wings to cover the needle. The forward end of the slot widens to a generally V-shaped mouth to facilitate the passage of the wings into the slot. The sheath may include a cutout in the body at the rearward end of the slot for receiving and engaging the wings to lock the body in its position covering the needle. In a second embodiment, the rearward edge of the wings and the forward edge of the sheath are configured to cooperate so that when the needle is pulled toward the sheath, the wings fold together to pass into the slot.

The improved IV infusion set of the present invention thus provides a sheath to cover the needle after it is used in order to reduce the risk of needlesticks with the used needle. The sheath is slidably disposed on the IV tubing so that it is readily available and easily operated. The IV infusion set preferably includes means for locking the sheath in its position covering the needle to prevent the sheath from being inadvertently removed. The improved IV infusion set can be constructed so that the needle can be retracted and locked into a protective sheath by pulling on the IV tube, without manipulating the needle.

BRIEF DESCRIPTION OF THE DRAWINGS

FIG. 1 is a side elevation view of a first embodiment of an IV infusion set constructed according to the principles of this invention, shown with the sheath locked in its position covering the needle;

FIG. 2 is a top plan view of the first embodiment as shown in FIG. 1;

FIG. 3 is a front end elevation of the first embodiment as shown in FIG. 1;

FIG. 4 is a front end elevation of the first embodiment, showing the wings passing through the slot in the sheath;

Corresponding reference characters indicate corresponding parts throughout the several views of the drawings.

DETAILED DESCRIPTION OF THE PREFERRED EMBODIMENTS

Figure 5:
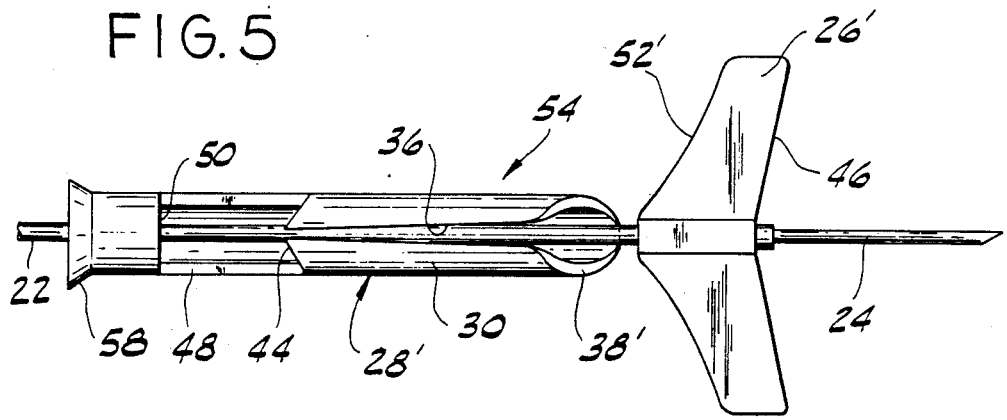
FIG. 5 is a top plan view of a second embodiment of an IV infusion set constructed according to the principles of this invention.

A first embodiment of an improved IV infusion set is indicated generally as 20 in FIGS. 1-4. The IV infusion set 20 is of the type comprising a section of tube 22 preferably made of clear flexible plastic, a hollow needle 24 preferable made of metal at one end of the tube, and two outwardly projecting flexible wings 26 preferably made of flexible plastic. The wings are located adjacent the needle. This type of IV infusion set is commonly referred to as a "butterfly" infusion set. As is well known, a connector (not shown in FIGS. 1-4) is disposed on the end of the tube 22 opposite the needle 24, for connecting the IV infusion set to the appropriate medical apparatus.

The improved IV infusion set 20 includes a sheath 28 slidably disposed on the tube 22. Although the sheath 28 is slidably disposed on the tube, before and during use of the infusion set the sheath 28 is behind wings 26 and thus the wings prevent the sheath from interfering with the needle when the IV infusion device is in use. Of course, some means for temporarily securing the sheath relative to the tube could also be used, as described below with respect to the second embodiment. The sheath 28 is adapted to be slid past the flexible wings 26 to cover the needle 24 after the needle has been used. The sheath 28 includes means for locking the sheath in its position covering the needle. This locking means preferably comprises means on the sheath for engaging the wings 26.

The sheath 28 preferably comprises a hollow generally tubular body 30 having a forward end 32 oriented toward the needle 24 and a rearward end 34 oriented away from the needle 24. The sheath is preferably made from a clear, stiff but resilient plastic. The body 30 has at least one longitudinally extending slot 36 extending from the forward end 32 of the body toward the rearward end 34. The slot 36 is adapted to receive the wings 26 to allow at least part of the sheath 28 to be slid past the wings to cover the needle 24. (There could be more than one slot—for example, there could be a slot on each side of the device for receiving one of the wings.) The width of the slot 36 generally narrows from the front to the back, and at its rearward end the width of the slot is preferably less than twice the thickness of the wings. As shown in FIG. 1, the top portion 38 of the front end 32 of the tube is sloped upwardly and rearwardly. As shown in FIG. 2, the mouth 40 of the slot 36 at the forward end widens into a "V" to facilitate the passage of the wings into the slot.

The body also includes a cutout 42 at the rearward end of the slot 36, adapted to receive and engage the wings to lock the sheath in its position covering the needle. The cutout has downwardly, forwardly sloped forward edges 44 for engaging the forward edges 46 of the wings. The sloped forward edges 44 direct the wings downwardly, trapping the wings in the vertices between the forward edges 44 and the bottom edges 48 of the cutout, and preventing the needle from sliding forwardly out of the sheath. The cutout also has rearward edges 50 for engaging the rearward edges 52 of the wings. The rearward edges 50 prevent the needle from being slid rearwardly out of the sheath.

The flexible wings 26 are easily folded together (see FIG. 4), and passed through the "V" shaped mouth 40 of the slot 36, and into the slot 36. The wings pass through the slot until they reach cutout 42, whereupon they are released. The sloped forward edges 44 of the cutout 42 can engage the forward edges 46 of the wings, and the rearward edges 50 of the cutout 42 can engage the rearward edges 52 of the wings to lock the sheath in its position covering the needle. Because of the sloped configuration of the forward edges 44 of the cutout 42, and the tapering configuration of the slot 36 (at its rearward end it is narrower than the thickness of the two wings), it is very difficult to manipulate the wings back into the slot to expose the needle.

Figure 6:
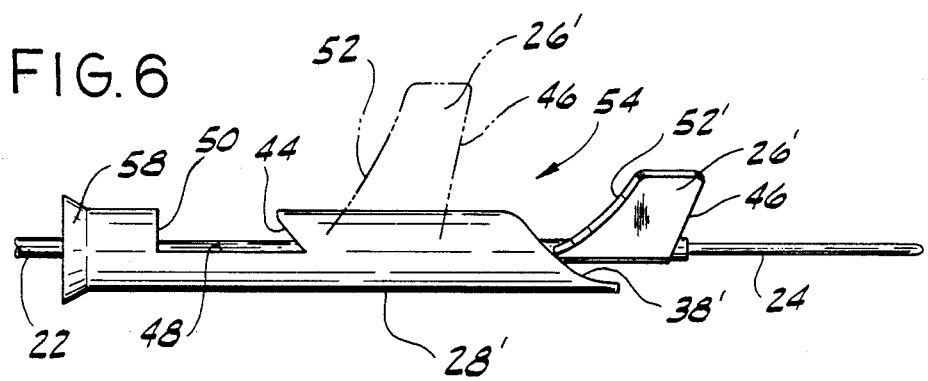
FIG. 6 is a side elevation view of the second embodiment as shown in FIG. 5.
Figure 7:
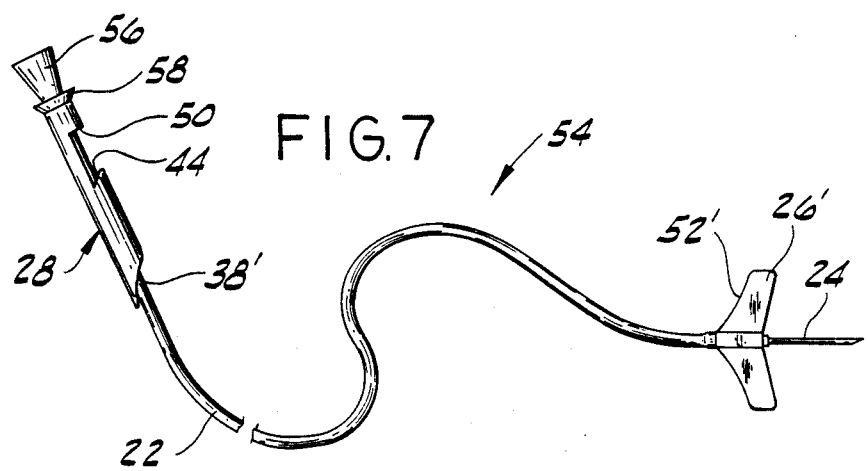
FIG. 7 is a plan view of the second embodiment showing the sheath engaged to the connector of the IV infusion set.

A second embodiment of an improved IV infusion set is indicated generally as 54 in FIGS. 5-7. The IV infusion set 54 is similar to IV infusion set 20 of the first embodiment, and corresponding parts are identified with corresponding reference numerals. The IV infusion set 58 comprises a section of tube 22, a hollow needle 24, and outwardly projecting flexible wings 26'. The wings 26' are similar to wings 26 of the first embodiment, except that the rearward edges 52' of the wings 26' are sloped generally forwardly and outwardly. In addition, the rearward edges 52' of the wings form smooth, continuous curves, with slight concavities. As shown in FIG. 7, the IV infusion set 54 includes a connector 56 at one end for connecting the infusion set to other medical apparatus.

The IV infusion set 54 also comprises a sheath 28' slidably disposed on the tube 22. The sheath 28' is similar to the sheath 28 of the first embodiment, except that the entire forward end 32' of the sheath 28' slopes generally upwardly and rearwardly. Furthermore, the forward end 32' of the sheath 28' forms a smooth, continuous curve with a slight concavity. The rearward end 34' of the sheath 28' has an outwardly flared portion 58. As best shown in FIG. 7, the flared portion 58 facilitates temporarily engaging the end of the sheath 28' on the connector 56 before and during use of the IV infusion set, so that the sheath 28' does not interfere with the use of the infusion set. The sheath 28' is preferably held by a friction or interference fit on the connector 56, although some other means of securing the sheath, such as a screw type fitting could be used. This feature could likewise be incorporated into the IV infusion set 20 of the first embodiment.

The rearward edges 52' of the wings 26' and the forward end 32' of the sheath 28' cooperate so that when the needle is pulled into the sheath, the wings are folded together and channeled into the slot. This permits the needle to be retracted into the sheath by simply pulling on the tubing, without manipulating the wings or otherwise handling the needle. It would even be possible to pull the needle directly from the patient into the sheath. The needle is retracted into the sheath until the wings 26' are engaged in the cutout 42, (just as the wings 26 are engaged in the cutout).

OPERATION

The use of the IV infusion device 20 of the first embodiment is no different than the use of a standard butterfly-type IV infuser. The infusion device is connected to an IV apparatus, and the needle placed in the patient. The wings 26 prevent the sheath 28 from interfering with the needle during use. When it is time to remove the IV infusion device 20, the device is removed in the same manner as a standard butterfly-type IV infuser. Then, the wings 26 are folded together, and the wings are aligned with the mouth 40 of slot 36 in the sheath, and the wings are slid into the slot 36. The width of the slot 36 tapers, but the resilience of the sheath permits the wings to be slid rearwardly to cutout 42. Once the wings 26 are in cutout 42, the wings are released and they resiliently unfold. The cutout 42 engages the wings 26, locking the sheath in its position over the needle. The sloped forward edges 44 and the tapering configuration of the slot 36 make it difficult to manipulate the wings back into the slot to remove the needle from the sheath. The sheathed, used needle can then be moved and disposed of with greatly reduced risk of needlesticks.

The infusion device 54 of the second embodiment is used like the infusion device 20 of the first embodiment. During use, the sheath 28' is held in place by its friction fit on connector 56. When it is time to remove the IV infusion device, the device can be removed in the same manner, or the sheath 28' can be released from the connector 56 and slid up to the rearward edge 52' of the wings 26' and the tube 22 pulled to simultaneously withdraw the needle from the patient and retract the needle into the sheath 28'. Pulling on the tube 22 pulls the rearward edges 52' of the wings 26' against the front end 32' of the sheath 28'. The smooth continuous curved configuration of these edges cams the wings 26' together, and channels the wings 26 into the slot 36. Pulling the tube further pulls the folded wings 26' through the slot 36 and into the cutout 42. Once in cutout 42 the wings unfold and are trapped in the cutout. The sheathed, used needle can then be moved and disposed of with greatly reduced risk of needlesticks.

With either embodiment, retracting the needle into the sheath is far preferable to trying to place a cap on the needle, which is the cause of numerous needlesticks with syringes, or simply leaving the needle uncovered.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. An improved IV infusion set of the type comprising a length of tube with a hollow needle at one end, and outwardly projecting flexible wings adjacent the end of the tubing with the needle, the improvement comprising:
a sheath slidably disposed on the tube and adapted to be slid over the needle to cover the needle after use, the sheath including means for locking the sheath in its position covering the needle to prevent needlesticks from the used needle, the means for locking the sheath comprising means on the sheath for engaging the wings.

2. The improved IV infusion set according to claim 1 wherein the sheath comprises a hollow generally tubular body having a forward end oriented toward the needle and a rearward end oriented away from the needle, the body having at least one longitudinally extending slot extending from the forward end of the body toward the rearward end, the slot adapted to receive the wings to allow at least part of the sheath to be slid past the wings to cover the needle.

3. The improved IV infusion set according to claim 2 wherein the forward end of the slot is widens to facilitate the passage of the wings into the slot.

4. The improved IV infusion set according to claim 2 wherein the sheath comprises a hollow generally tubular body having a forward end oriented toward the needle and a rearward end oriented away from the needle, the body having a slot extending longitudinally from the forward end of the body partway toward the rearward end, the slot adapted to receive the wings to allow at least part of the sheath to be slid past the wings to cover the needle, and a cutout in the body at the rearward end of the slot the cutout adapted to receive and engage the wings to lock the body in its position covering the needle.

5. The improved IV infusion set according to claim 4 wherein the width of the slot at the rearward end is less than the thickness of the wings to resist retraction of the sheath from it position covering the needle.

6. The improved IV infusion set according to claim 1 further comprising means for temporarily securing the sheath relative to the tube.

7. The improved IV infusion set according to claim 6 further comprising a connector on the end of the tube, and where the means for temporarily securing the sheath comprises means for frictionally engaging the connector.

8. An improved IV infusion set of the type comprising a length of tube with a hollow needle at one end and outwardly projecting flexible wings between the needle and the length tube, the improvement comprising:
a sheath slidably disposed on the tube before and during use of the infusion set and adapted to be slid past the wings to cover the needle after use, the sheath including means for locking the sheath in its position covering the needle to prevent needlesticks from the used needle, the means for locking the sheath comprising means on the sheath for engaging the wings.

9. The improved IV infusion set according to claim 8 wherein the sheath comprises a hollow generally tubular body having a forward end oriented toward the needle and a rearward end oriented away from the needle, the body having at least one longitudinally extending slot extending from the forward end of the body toward the rearward end, the slot adapted to receive the wings to allow at least part of the sheath to be slid past the wings to cover the needle.

10. The improved IV infusion set according to claim 9 wherein the forward end of the slot is widens to facilitate the passage of the wings into the slot.

11. The improved IV infusion set according to claim 8 wherein the sheath comprises a hollow generally tubular body having a forward end oriented toward the needle and a rearward end oriented away from the needle, the body having a slot extending longitudinally from the forward end of the body partway toward the rearward end, and a cutout in the body at the rearward end of the slot, the slot adapted to allow the wings to pass to the cutout to allow at least a portion of the sheath to slide past the wings to cover the needle, the cutout engaging the wings and locking the body in its position covering the needle.

12. The improved IV infusion set according to claim 11 wherein the forward end of the slot is widens to facilitate the passage of the wings into the slot.

13. The improved IV infusion set according to claim 11 wherein the cutout has front edges for engaging the front edges of the wings and rear edges for engaging the rear edges of the wings, and wherein the front edges slope forwardly, to engage the wings.

14. The improved IV infusion set according to claim 11 wherein the width of the slot diminishes from the front to the back.

15. The improved IV infusion set according to claim 14 wherein the width of the slot at the rearward end is less than the thickness of the wings to resist retraction of the sheath from it position covering the needle.

16. An improved IV infusion set of the type comprising a length of tube with a hollow needle at one end and outwardly projecting flexible wings between the needle and the length tube, the wings having forward edges oriented toward the needle and rearward edges oriented away from the needle, the improvement comprising:
a sheath slidably disposed on the tube before and during use of the infusion set, the wings and the sheath adapted to cooperate so that at least a portion of the sheath can slide past the wings to cover the needle when the tube is pulled rearwardly to retract the needle into the sheath.

17. The improved IV infusion set according to claim 16 wherein the sheath comprises a hollow generally tubular body having a forward end oriented toward the needle and a rearward end oriented away from the needle, the body having a slot extending longitudinally from the forward end of the body partway toward the rearward end, and a cutout in the body at the rearward end of the slot, the slot adapted to allow the wings to pass to the cutout to allow at least a portion of the sheath to slide past the wings to cover the needle, the cutout engaging the wings and locking the body in its position covering the needle, the forward end of the slot widening to receive the wings and the rearward edges of the wings slope generally forwardly and outwardly so that when the needle is pulled into the sheath the mouth of the slot and the shape of the rearward edges of the wings cooperate to fold the wings together so that they pass into the slot.

18. An improved IV infusion set of the type comprising a length of tube with a hollow needle at one end and outwardly projecting flexible wings between the needle and the length tube, the wings having forward edges oriented toward the needle and rearward edges oriented away from the needle, the improvement comprising:

a sheath comprising a hollow generally tubular body having a forward end oriented toward the needle and a rearward end oriented away from the needle, the body having a slot extending longitudinally from the forward end of the body partway toward the rearward end, and a cutout in the body at the rearward end of the slot, the slot adapted to allow the wings to pass to the cutout to allow at least a portion of the sheath to slide past the wings to cover the needle, the cutout engaging the wings and locking the body in its position covering the needle, the forward end of the slot having a outwardly widening mouth and the rearward edges of the wings being configured to cooperate with the mouth of the slot so that when the needle is pulled toward the sheath, the wings fold together to pass into the slot.

19. The improved IV infusion set according to claim 18 wherein the rearward edges of the wings slope taper inwardly in the rearward direction.

* * * * *